United States Patent [19]

Taylor

[11] Patent Number: 5,002,070
[45] Date of Patent: * Mar. 26, 1991

[54] LAUNDERABLE CLOTH-LIKE PRODUCT FOR SURGICAL USE AND METHOD OF MAKING THE SAME

[75] Inventor: Jeffrey L. Taylor, Cincinnati, Ohio

[73] Assignee: Standard Textile Company, Inc., Cincinnati, Ohio

[*] Notice: The portion of the term of this patent subsequent to Dec. 31, 2002 has been disclaimed.

[21] Appl. No.: 133,306

[22] Filed: Dec. 16, 1987

Related U.S. Application Data

[60] Continuation of Ser. No. 793,911, Nov. 1, 1985, abandoned, which is a division of Ser. No. 529,475, Sep. 6, 1983, Pat. No. 4,561,434.

[51] Int. Cl.$^5$ .............................................. A61F 13/00
[52] U.S. Cl. ................................. 128/853; 428/252; 128/156
[58] Field of Search ..................... 128/849, 853, 854; 428/252, 245

[56] References Cited

U.S. PATENT DOCUMENTS

| | | | |
|---|---|---|---|
| 3,182,656 | 5/1965 | Pyne | 128/853 |
| 3,364,928 | 1/1968 | Creager, Jr. et al. | 128/853 |
| 3,426,185 | 12/1975 | Krzewinski | 128/854 |
| 3,667,458 | 6/1972 | Krebs | 128/853 |
| 3,856,006 | 12/1974 | Krzewinski | 128/854 X |
| 3,910,268 | 10/1975 | Miller | 128/854 |
| 3,930,497 | 1/1976 | Krebs et al. | 128/853 |
| 4,196,723 | 4/1980 | Moose, Jr. | 128/854 |
| 4,286,012 | 8/1981 | Zins et al. | 428/252 |
| 4,316,456 | 2/1982 | Stoneback | 128/852 |
| 4,336,797 | 6/1982 | Latucca et al. | 128/854 |
| 4,561,434 | 12/1985 | Taylor | 128/849 |

Primary Examiner—Randolph A. Reese
Assistant Examiner—Jeffrey L. Thompson
Attorney, Agent, or Firm—Kinney & Schenk

[57] ABSTRACT

A launderable cloth-like product for surgical use and method of making same are provided wherein such product has a plurality of layers comprising at least a portion thereof with the plurality of layers comprising a bottom layer and a top layer each made of woven material and the layers are suitably fastened together. The top layer is made with warps and wefts in a plain weave with each of the warps and wefts being made of a blend of natural material and synthetic material and a coating on the top layer defines the outside surface thereof. The coating has hydrophobic properties such that the top layer when new and with the coating thereon is substantially impermeable to water flow therethrough prior to laundering thereof and when subjecting the outside surface to a hydrostatic water pressure generally of the order of 50 pounds per square inch gauge.

3 Claims, 2 Drawing Sheets

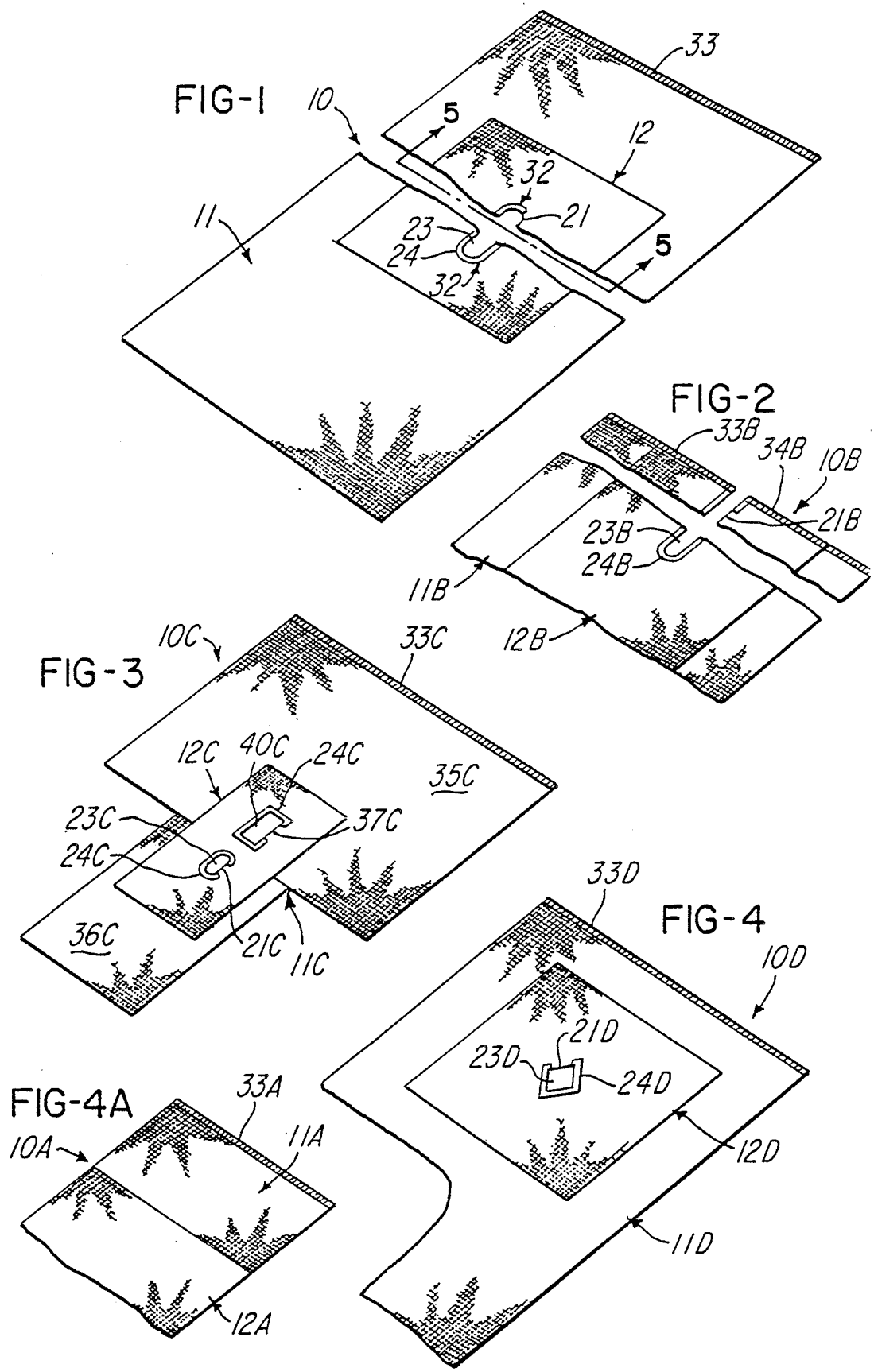

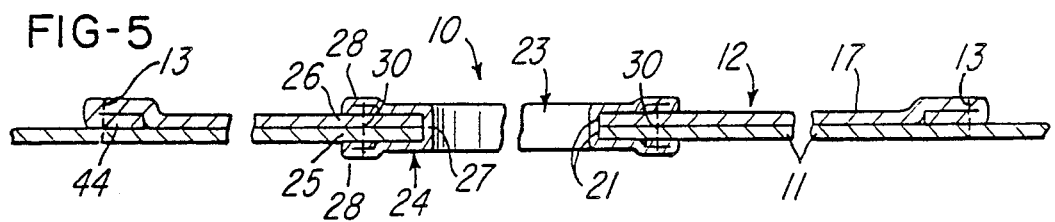
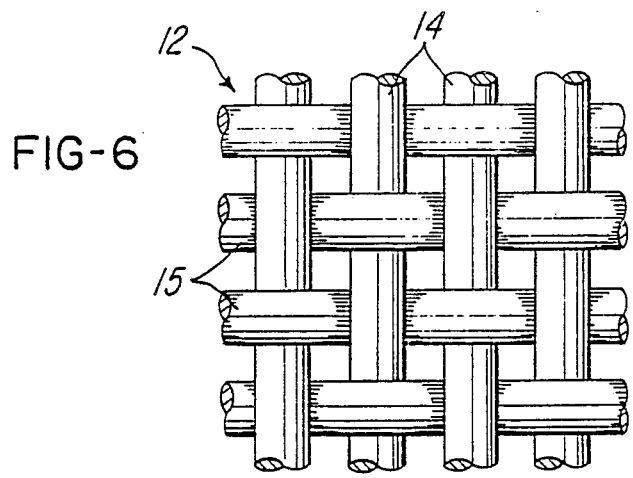
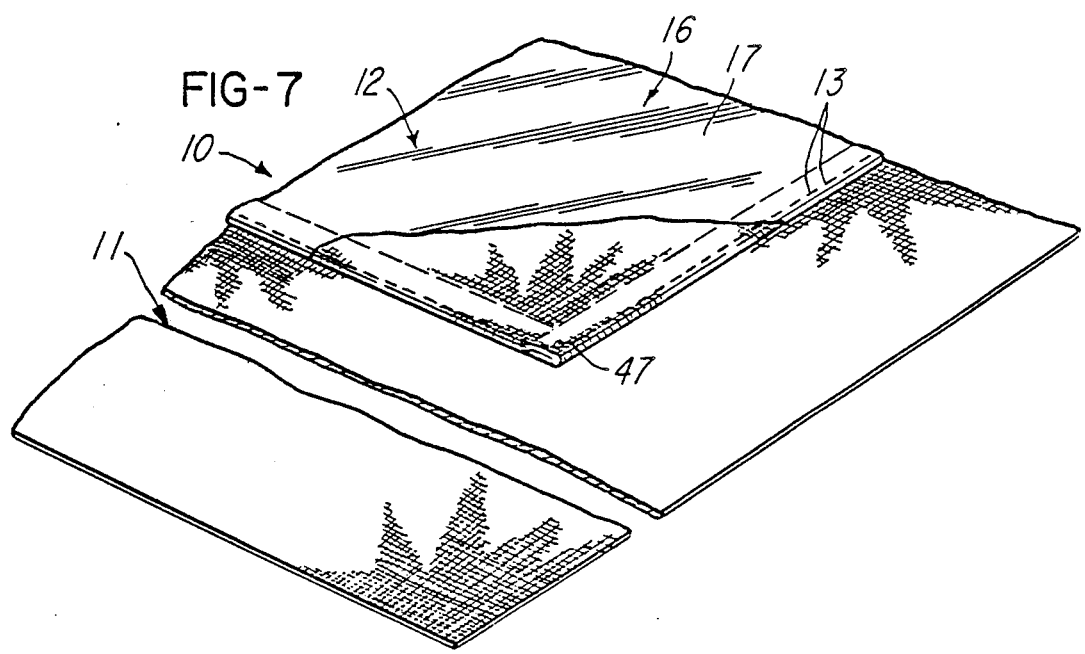

LAUNDERABLE CLOTH-LIKE PRODUCT FOR SURGICAL USE AND METHOD OF MAKING THE SAME

This is a continuation of application Ser. No. 793,911 filed Nov. 1, 1985, which in turn is a division of application Ser. No. 06/529,475, now U.S. Pat. No. 4,561,434.

BACKGROUND OF THE INVENTION

1. Field of the Invention

This invention relates to a launderable cloth-like product for surgical use and method of making same and in particular to such a product in the form of a surgical drape or surgical cover.

2. Prior Art Statement

During surgical procedures, use is made of surgical gowns, drapes, and covers. It is especially important, in what is referred to as the critical surgical zone, that the drapes and covers be essentially impermeable to liquids, be low linting, and have no tendency to build up a charge of static electricity. Each cover is employed to prevent bacteria from moving from its table to operating instruments and equipment supported thereon. Each drape is employed to protect the patient and such protection includes protection against movement of bacteria to the surgical incision on the patient. The critical surgical zone is defined as an area within approximately 10 inches of a fenestration in a surgical drape, the to surface of a back table where packs are opened and instruments laid out for surgery and the table portion of what is commonly referred to as a Mayo Stand.

It is known in the art to provide a launderable cloth-like product for surgical use, such as a gown, drape, or cover which may be comprised of a single layer or a plurality of layers on at least a portion thereof.

It is also known in the art to provide such a surgical product comprised of single layer of fabric formed of cotton fibers. It is also known to provide such a surgical product consisting of two layers of fabric each formed from all cotton fibers, or one layer of fabric formed of all cotton fibers and one layer of fabric formed of a blend of polyester and cotton fibers.

However, considering only surgical drapes and covers, for example, some of the previously proposed surgical drapes and covers, particularly those made predominately of natural fibers, such as cotton, generally tend to lint. Further, prior surgical drapes and covers made predominately of natural fibers have what is often referred to as memory, i.e., such prior drapes and covers tend to inherit creases sooner and retain creases for longer periods of time, which is undesirable. In addition, each of the abovementioned surgical products proposed heretofore also have poorer hydrophobic properties, i.e., a tendency to repel water more poorly, especially after extended use.

In an effort to improve the hydrophobic properties of previously proposed surgical drapes and covers it has been proposed heretofore to provide an outside layer in each surgical drape and cover which is made of a woven material having generally of the order of 216 warps and wefts per square inch thereof. However, with such a high count of warps and wefts per square inch the cost of the material is very high whereby such material tends to be less competitive.

Thus, it is apparent that previously proposed surgical products, such as surgical drapes and covers have certain deficiencies.

SUMMARY OF THE INVENTION

This invention provides an improved launderable cloth-like product for surgical use which overcomes the above-mentioned deficiencies. The improved product of this invention has a plurality of layers comprising at least a portion thereof with such plurality of layers comprising a bottom layer and a to player each made of woven material and means fastening the layers together.

In accordance with one embodiment of this invention the top layer of the above-mentioned product is made with warps and wefts in a plain weave and each of the warps and wefts is made of a blend of natural material and synthetic material and coating means is provided on the top layer defining the outside surface thereof. The coating means has hydrophobic properties such that the top layer when new and with the coating means thereon is substantially impermeable to water flow therethrough prior to laundering thereof and when subjecting the outside surface to a hydrostatic water pressure generally of the order of 50 pounds per square inch gauge.

In accordance with another embodiment of this invention a launderable cloth-like surgical drape is provided which has a plurality of layers comprising at least a portion thereof and the plurality of layers comprise a bottom layer and a top layer each made of woven material with means fastening the layers together. The surgical drape has a pair of substantially identical aligned openings in the layers which define a fenestration in the drape which is useable during surgery. The top layer of the surgical drape is made with warps and wefts in a plain weave and each of the warps and wefts is made of a blend of natural material and synthetic material and coating means provided on the top layer defines the outside surface thereof. The coating means has hydrophobic properties so that the top layer when new and with the coating means thereon is substantially impermeable to water flow therethrough prior to laundering thereof and when subjecting the outside surface of the to player to hydrostatic water pressure generally of the order of 50 pounds per square inch gauge.

Accordingly, it is an object of this invention to provide an improved launderable cloth-like product of the character mentioned for surgical use.

Another object of this invention is to provide such a product in the form of a surgical drape.

Another object of this invention is to provide such a product in the form of a surgical cover.

Another object of this invention is to provide an improved method of making a launderable cloth-like product of the character mentioned for surgical use.

Other features, objects, uses, and advantages of this invention are apparent from a reading of this description which proceeds with reference to the accompanying drawings forming a part thereof.

BRIEF DESCRIPTION OF THE DRAWINGS

The accompanying drawings show present preferred embodiments of this invention, in which FIG. 1 is an isometric view with the central portion thereof broken away illustrating one exemplary embodiment of a launderable cloth-like product for surgical use which is in the form of a surgical drape;

FIG. 2 is a view similar to FIG. 1 illustrating another exemplary embodiment of a surgical drape;

FIG. 3 is an isometric view illustrating still another exemplary embodiment of a surgical drape;

FIG. 4 is a view with an end portion broken away illustrating yet another exemplary embodiment of a surgical drape;

FIG. 4A is a view drawn to a reduced scale showing an exemplary launderable cloth-like product in the form of a surgical cover;

FIG. 5 is an enlarged cross-sectional view taken essentially on line 5—5 of FIG. 1;

FIG. 6 is a greatly enlarged fragmentary plan view particularly illustrating the weave of a typical top layer which comprises each of the exemplary products of FIGS. 1, 2, 3, 4, and 4A disclosed herein; and FIG. 7 is an enlarged fragmentary isometric view of a typical portion of a surgical drape which is essentially the same for the drapes of FIGS. 1–4 and would be similar for the cover of FIG. 4A, and particularly showing the manner of fastening of the top layer in position and coating means on such top layer.

DETAILED DESCRIPTION

Reference is now made to FIG. 1 of the drawings which illustrates one exemplary embodiment of a launderable cloth-like product for surgical use and the product of FIG. 1 is in the form of a surgical drape which is designated generally by the reference numeral 10. The drape has a plurality of layers comprising at least a portion thereof and in this example such plurality of layers comprises a bottom layer 11 and a top layer 12 each made of woven material and means, shown in FIG. 5 as fastening threads 13, fastening the layers 11 and 12 together.

As emphasized in the enlarged view of FIG. 6, which illustrates a typical top layer, such as the top layer 12 of FIG. 1, such top layer is made of a plurality of warps 14 disposed in substantially equally spaced apart parallel relation and a plurality of wefts 15 also disposed in substantially equally spaced apart parallel relation with the warps 14 and wefts 15 being woven in a plain weave and such plain weave is well known in the art. Each of the warps 14 and wefts 15 is made of a blend of natural material and synthetic material and preferably the natural material is in the form of cotton and the synthetic material is in the form of polyester.

In accordance with the teachings of this invention, coating means, shown as a coating 16 in FIG. 7, is provided on the to player 12 and defines the outside surface 17 of such top layer. The coating means or coating 16 has hydrophobic properties and the to p layer 12 with the coating 16 is substantially impermeable to water flow therethrough prior to laundering thereof and when subjecting the outside surface 17 to a static water pressure generally of the order of 50 pounds per square inch gauge (psig).

The above description has emphasized the impermeable character of the top layer with its coating 16 thereon prior to laundering thereof; however, after approximately 100 so-called institutional laundry cycles the top layer 12 with the coating 16 is substantially impermeable to water flow therethrough when subjecting the outside surface 17 to a static water pressure generally of the order of 25 psig wherein each institutional laundry cycle comprises washing, drying, and steam sterilization. It will be appreciated that an institutional laundry cycle refers to a laundry cycle as would be typical at a hospital, nursing home, rest home, clinic, commercial laundry or the like.

The coating 16 has been described as a coating having hydrophobic properties; however, it will also be appreciated that the coating 16 is also of the type which resists buildup of static electricity thereon.

As previously mentioned each of the warps 14 and wefts 15 is made of a blend of natural material and synthetic material and preferably such blend is a blend ranging between 40% synthetic material and 60% natural material and 50% synthetic material and 50% natural material. A blend defining the warps 14 and wefts 15 within the range indicated assures adherence of the coating 16 thereto with optimum tenacity due to the presence of a substantial portion of the natural material therein, yet such blend provides a high-strength substantially non-linting character to the top layer 12 due to the presence of synthetic material therein. The preferred natural material is cotton and the preferred synthetic material is polyester with the cotton being comprised of staple cotton fibers.

As described above, the top layer 12 with the coating 16 thereon is substantially impermeable to water flow therethorugh under the specified conditions. This is due, in part, to the tightness of weave of the top layer. However, it will be appreciated that it is important that the weave not be too tight such that it has too many warps 14 and wefts 15 per square inch so as not to increase the cost of the woven top layer or fabric unnecessarily, even though it may be provided with coating means 16 thereon. In particular, it is preferred that the top layer has no less than 165 warps and wefts per square inch and preferably such top layer has between 165 and 200 warps and wefts per square inch.

Thus, with the top layer 12 being made using a blend of cotton fibers or filaments and polyester fibers or filaments in its warps and wefts and having a density per square inch, as indicated above, and with such layer 12 being provided with coating 16 which has both hydrophobic properties and prevents buildup of static electricity thereon, such layer 12 is stronger and more resistant to abrasion, has less tendency to lint, has less memory which results in a smaller number of permanent-type creases, and maintains its finish better. In addition, the layer 12 has a greater tendency to repel water or aqueous fluids of all types including saline water, blood, and the like even after a substantial number of institutional laundry cycles and as specifically set forth above.

As previously mentioned, the launderable cloth-like product 10 of FIG. 1 is in a form of a surgical drape and such surgical drape has a pair of substantially identical aligned openings therein shown as an opening 21 in the bottom layer 11 and an opening in the top layer 12 which is also designated by the reference numeral 21 and is shown best in FIG. 5. The aligned openings 21 define an aperture which will be referred to as a fenestration 23 in the drape and the fenestration 23 is useable during surgery.

The surgical drape 10 also has what will be referred to as a fabric tape 24 disposed around the fenestration 23 and the tape 24 is sewn to portions 25 and 26 of the layers 11 and 12 respectively which adjoin such fenestration 23. Once sewn into position, the tape 24 has a substantially U-shaped cross-sectional configuration defined by a bight 27 and a pair of legs 28 extending in parallel relation from the bight 27. The U-shaped cross-sectional configuration is provided about the entire periphery of the fenestration 23 and hence at each location around such periphery.

The openings 21 defined in the layers 11 and 12 are die-cut openings and thus made with great precision. In particular, it will be appreciated that the openings 21 are defined in a simultaneous manner with the layer 12 sewn in position on layer 11 and using a male cutting die urging the layers 11-12 against a flat cutting surface (not shown) to define both of the openings. The male die used to provide the die-cut openings 21 may be any suitable die known in the art which is capable of cutting fabric layers of the type disclosed herein.

As seen in FIG. 1 the bottom layer 11 is comparatively large in area and the top layer 12 is substantially smaller in area than the area of the bottom layer 11. The top layer 12 has its peripheral edges disposed remote from the peripheral edges of the bottom layer. In particular, in the surgical drape 10 of FIG. 1 the top layer 12 is substantially centrally disposed within the peripheral outline of the bottom layer 11. In addition, the aligned openings 21 defining the fenestration 23 are also disposed in the central portion of the top layer 12.

The openings 21 may have any desired configuration; however, in this example of the invention such aligned openings have curved portions shown at two locations 32 which define corresponding curved portions of the fenestration 23. The curved portions at 32 in this example of the invention are semicircular and are adjoined by straight parallel sides whereby the aligned openings 21 and fenestration 23 have an oval configuration.

The surgical drape 10 also has a red border 33 which defines the head end of such drape. The red border is indicated by the appropriate drafting symbol for red and it will be appreciated that such red border 33 may be defined by a red binding tape which is suitably sewn in position, or other suitable known means.

The surgical drape of this invention may have any suitable configuration depending upon the intended surgical use. The drape 10 of FIG. 1 is considered a laparotomy drape.

Another exemplary embodiment of a launderable cloth-like product for surgical use is illustrated in FIG. 4A of the drawings and such product is in the form of a surgical cover and is designated by the reference numeral 10A. The cover 10A is what is referred to as a non-fenestrated cover and has a plurality of layers comprising the major portion thereof and the plurality of layers in this example comprises a bottom layer 11A, a to player 12A, and means for fastening the layers together and such means is preferably in the form of stitch means of any type known in the art. The cover 10A has a red border 33A at one end thereof which is made in a similar manner as the border 33 and thus border 33A will not be described in detail herein.

As disclosed above, the surgical drape 10 is a particular type of surgical drape and the surgical cover 10A is also of a particular configuration. However, it will be appreciated that the teachings of this invention are fully applicable to other types of surgical drapes and other types of surgical covers other than the drape 10 and the cover 10A.

For example, other exemplary embodiments of the surgical drape of this invention are illustrated in FIGS. 2, 3, and 4. The surgical drapes illustrated in FIGS. 2, 3, and 4 are very similar to the surgical drape 10. Therefore, such surgical drapes will be designated generally by the reference numerals 10B, 10C, and 10D respectively and representative parts of each surgical drape which are similar to corresponding parts of the surgical drape 10 will be designated in the drawings by the same reference numeral as the surgical drape 10 (whether or not such representative parts are mentioned in the specification) followed by the associated letter designation B, C, or D not described again in detail. Only those component parts of each surgical drape of FIGS. 2, 3, and 4 which are substantially different from corresponding parts of the surgical drape 10 will be designated by a new reference numeral also followed by the associated letter designation and described in detail.

The surgical drape 10B of FIG. 2 has a bottom layer 11B which is comparatively large in area and the top layer 12B is smaller in area than the are of the bottom layer 11B; however, in the drape 10B the top layer 12B is disposed with an edge thereof in alignment with an edge of the bottom layer as shown at 34B. In addition, the aligned openings 21B in the drape 10B are substantially U-shaped die-cut openings 21B which are disposed in layers 11B and 12B so that the open ends thereof coincide with the edges at 34B. In this manner the aligned openings 21B define a U-shaped fenestration 23B having an open end and a tape 24B is sewn therearound.

The surgical drape 10B may, depending on the overall size thereof and the length of its U-shaped fenestration 23B, be in the form of a split drape or a head drape. However, regardless of type, the drape 10B is provided with a red border 33B at the head end thereof.

The surgical drape 10C of FIG. 3 has a roughly T-shaped bottom layer which is designated by the reference numeral 11C and is made of a plurality of two parts 35C and 36C. The two parts 35C and 36C of this example consist of the crossarm portion 35C of the T-shape and the leg portion 36C which are suitably fastened together in side-by-side relation, as by sewing, or the like. In the drape 10C the top layer 12C thereof straddles the pair of parts 45C and 36C of its bottom layer 11C.

The surgical drape 10C has a pair of die-cut aligned oval openings 21C disposed in a central portion of the top layer 12C and in the bottom layer 11C. The drape 10C also has a second pair of die-cut aligned rectangular openings 37C disposed in the central portion of the top layer 12C and in the bottom layer 11C. The openings 37C are disposed in spaced relation from the first-named pair of aligned openings 21C. The first pair of openings 21C define a fenestration 23C and the second pair of openings 37C define a second fenestration 40C in the drape 10C.

The openings 21C have a tape 24C sewn therearound while the openings 37C also have a substantially identical tape, also designated by the reference numeral 24C, sewn therearound. The surgical drape 10C also has a red border 33C defining the head portion thereof and it will be appreciated that the surgical drape 10C is a laparoscopy drape.

The surgical drape 10D of FIG. 4 has a bottom layer 11D and a top layer 12D and the drape 10D has a pair of die-cut aligned openings 21D in the layers 11D and 12D and disposed in the central portions of such layers. The aligned openings 21D are of polygonal outline and define a fenestration 23D of corresponding polygonal outline. In this example, the openings 21D and fenestration 23D are of rectangular outline and in the form of a square. The surgical drape 10D also has a tape 24D outlining the fenestration 23D.

The drape 10D is typical of what is referred to as a thyroid drape. Further, the surgical drape 10D has a red border 33D defining the head thereof.

The tapes 24, 24B, 24C, and 24D are all preferably bias tapes preferably made of the same material as their corresponding top layers 12, 12B, 12C, and 12D and each of such tapes also preferably has a coating 16 provided thereon. It will also be appreciated that each of the tapes 24, 24B, 24C, and 24D may be fastened in position by any suitable means, such as, suitable thread means or fastening threads. A typical fastening thread for fastening tape 24 in position is illustrated in connection with the surgical drape 10 of FIG. 1 and such thread or stitching is designated generally by the reference numeral 30 in FIG. 5.

As mentioned earlier, the surgical drapes illustrated in this disclosure of the invention are only exemplary types of drapes and it is to be understood that other types of surgical drapes may be made using the teachings of this invention, provided that the unique top layer similar to top layer 12 has coating 16 provided thereon. The layer 12 of surgical drape 10 is basically provided in the critical zone for surgery which is defined as the area within 10 inches of any fenestration in the surgical drape as mentioned earlier.

In the case of a surgical cover, such as cover 10A, it will be appreciated that the cover 10A is constructed such that the layer 12A thereof has coating means thereon similar to coating 16. The critical zone for surgery includes the top surface of a back table where packs are opened and instruments laid out for use during surgery and cover 10A would be used on such back table.

The top layers 12, 12A, 12B, 12C, and 12D are preferably fastened in position using any suitable fastening means and such top layers are fastened in position as shown typically in FIGS. 5 and 7 for drape 10 by turning peripheral outer edges thereof inwardly and under as shown at 44 in FIG. 5 and then sewn in position by stitch means or stitches 13. The sewing action at each corner is in the form of a loop in the stitch means 13, as shown at 47 in FIG. 7.

The coating means or coating 16 may be any suitable coating known in the art and a typical coating which may be utilized is known as a QUARPEL coating or finish and is in the form of a moisture repellant finish which also tends to resist the buildup of static electricity. QUARPEL coating or finish is marketed by the Reese Brothers, Bishopville, South Carolina; and Delta Finish, Wallace, South Carolina.

The fabric material defining the bottom layers 11 and 11A, 11B 11C, and 11D is preferably a plainwoven material consisting of 50% combed cotton percale and 50% polyester with the warps and wefts thereof being made of a blend of 50% combed cotton percale and 50% polyester. The material of layers 11 and 11A–11D is preferably provided with an antistatic permanent press finish.

The top layers 12, 12A, 12B, 12C, and 12D are each made in a plainwoven weave with each warp and weft thereof being made by a blend of a natural material and a synthetic material and preferably a blend of cotton and polyester in the ranges previously specified for the top layer 12 and as described in connection with FIG. 6 of the drawings. It will be appreciated that the description of the layer 12 if fully applicable to the layers 12A, 12B, 12C, and 12D and thus will not be repeated.

The material defining the layer 12 or layers 12A through 12D is available commercially from two sources. One source is the J. P. Stevens Company, Stevens Towers, 1185 Avenue of the Americas, New York, New York 10036 and such material with the film 16 thereof is referred to as Barrier 4101. The other source is L. Travis Textiles, a division of Putnam Mills Corporation, 49 West 37th Street, New York, New York 10018. L. Travis Textiles buys basic plainwoven material in a greige sate and then applies the QUARPEL coating thereon. L. Travis Textiles identifies the product as Style 3482.

However, it will be appreciated that regardless of the source of purchase of materials defining the top and bottom layers and regardless of whether such materials are used to make a surgical cover or a surgical drape, the teachings of this invention are employed to define an improved launderable cloth-like product for surgical use.

The performance characteristics of the articles consisting of the various surgical drapes 10B, 10C, and 10D and of surgical cove 10A are substantially identical to the performance characteristics of the surgical drape 10 and such performance characteristics will not be repeated. In addition, it will be appreciated that the performance of each of these articles will be essentially the same afte subjecting same to 100 institutional laundry cycles in the manner defined above.

In this disclosure of the invention the top layer in each instance is fastened in position by sewing and with a particular stitch after folding peripheral portions of each to player inwardly in position as shown in FIG. 7. However, it will be appreciated that the fastening means may be any suitable means known in the art and the sewing may not necessarily be by stitches of the type shown but may be any other suitable stitch.

In this disclosure of the invention use has been made of terms such as top, bottom, side, and the like. However, it is to be understood that these terms are used to describe the items as illustrated in the drawings and such terms are not to be considered limiting in any way.

While present exemplary embodiments of this invention and methods of practicing the same, have been illustrated and described, it will be recognized that this invention may be otherwise variously embodied and practiced within the scope of the following claims.

What is claimed is;

1. In a launderable cloth-like product for use as a surgical drape or a surgical cover and having a plurality of layers comprising at least a portion thereof; said plurality of layers comprising a bottom layer and a top layer each made of woven material; and means fastening said layers together, the improvement in which said top layer is made with between a total of 165 and 200 warps and wefts per square inch in a plain weave, each of said warps and wefts being made of a blend of natural material and synthetic material, said top layer having substantially its entire area which is disposed within its peripheral outline overlying a corresponding area of said bottom layer to define at least a double thickness in said drape or cover throughout the top layer area of said drape or cover, and coating means only on said top layer defining the outside surface thereof, said fastening means being in the form of stitches, said coating means having hydrophobic properties and also serving to resist buildup of static electricity, said top layer with said coating means thereon being substantially impermeable to water flow therethrough prior to laundering thereof when subjecting said outside surface to a hydrostatic water pressure generally of the order of 50 psig, said between a total of 165 and 200 warps and wefts per square inch serving to minimize the cost of said woven top layer yet being sufficient to define a tight weave, said top layer with said coating means being substantially impermeable to water flow therethrough when subjecting said outside surface to a hydrostatic water pressure generally of the order of 25 psig after approximately 100 institutional laundry cycles wherein each of said laundry cycles comprises washing, drying, and steam sterilization, said blend being a blend ranging between 40 percent synthetic material and 60 percent natural material and 50 percent synthetic material and 50 percent natural material, said blend assuring adherence of said coating means with optimum tenacity yet providing a high-strength substantially nonlinting top layer, said top layer having substantially an equal number of warps and wefts per square inch.

2. A product as set forth in claim 1 in which said top layer has a peripheral outer edge turned inwardly and under adjoining portions of said top layer, and said stitches extend through said inwardly turned outer edge.

3. A product as set forth in claim 1 in which said natural material is cotton and said synthetic material is polyester.

* * * * *